United States Patent
Reiner

(10) Patent No.: US 7,607,079 B2
(45) Date of Patent: Oct. 20, 2009

(54) MULTI-INPUT REPORTING AND EDITING TOOL

(76) Inventor: Bruce Reiner, 6 Greenleaf La., Seaford, DE (US) 19973

( * ) Notice: Subject to any disclaimer, the term of this patent is extended or adjusted under 35 U.S.C. 154(b) by 0 days.

(21) Appl. No.: 11/806,596

(22) Filed: Jun. 1, 2007

(65) Prior Publication Data

US 2007/0237378 A1 Oct. 11, 2007

Related U.S. Application Data

(60) Provisional application No. 60/809,823, filed on Jun. 1, 2006.

(51) Int. Cl.
G06F 17/00 (2006.01)

(52) U.S. Cl. .................. 715/233; 715/230; 715/231; 715/268; 345/619; 382/132

(58) Field of Classification Search ......... 715/230–234; 600/407; 382/128, 132; 345/619
See application file for complete search history.

(56) References Cited

U.S. PATENT DOCUMENTS

| | | | |
|---|---|---|---|
| 4,974,194 A | 11/1990 | Barker | |
| 5,148,366 A | 9/1992 | Buchanan et al. | |
| 5,267,155 A | 11/1993 | Buchanan et al. | |
| 5,522,022 A | 5/1996 | Rao et al. | |
| 5,586,239 A | 12/1996 | Ueda | |
| 5,615,284 A * | 3/1997 | Rhyne et al. | 382/187 |
| 5,768,418 A | 6/1998 | Berman et al. | |
| 5,782,762 A | 7/1998 | Vining | |
| 5,832,474 A | 11/1998 | Lopresti et al. | |
| 5,838,313 A * | 11/1998 | Hou et al. | 715/201 |
| 5,884,256 A | 3/1999 | Bennett et al. | |
| 5,890,177 A | 3/1999 | Moody et al. | |
| 5,897,648 A | 4/1999 | Henderson | |
| 5,982,953 A * | 11/1999 | Yanagita et al. | 382/294 |
| 5,987,345 A * | 11/1999 | Engelmann et al. | 600/407 |
| 6,057,845 A | 5/2000 | Dupouy | |
| 6,083,162 A | 7/2000 | Vining | |
| 6,173,068 B1 * | 1/2001 | Prokoski | 382/115 |
| 6,366,683 B1 | 4/2002 | Langlotz | |
| 6,542,579 B1 | 4/2003 | Takasawa | |
| 6,567,549 B1 | 5/2003 | Marianetti, II et al. | |
| 6,681,372 B2 | 1/2004 | Yajima | |
| 6,687,876 B1 | 2/2004 | Schilit et al. | |
| 6,687,878 B1 * | 2/2004 | Eintracht et al. | 715/201 |
| 6,694,163 B1 | 2/2004 | Vining | |
| 6,721,452 B2 | 4/2004 | Confer et al. | |

(Continued)

OTHER PUBLICATIONS

Bottoni et al.,"Madcow: a Multimedia Digital Annotation System," presented AVI'04 May 25-28, 2004, ACM, pp. 55-62.*

(Continued)

Primary Examiner—Doug Hutton
Assistant Examiner—James H Blackwell
(74) Attorney, Agent, or Firm—Jean C. Edwards, Esq.; Akerman Senterfitt

(57) ABSTRACT

The present invention relates to a multi-input reporting and editing tool, which performs as a dynamic instrument to allow multiple users' input into creating a report, such that end-users may accumulate, process, and analyze information, in a timely, efficient, and accurate fashion. The multi-input reporting and editing tool allows tracking of follow-up data over time, and creates a vehicle for database mining and quality assessment.

34 Claims, 4 Drawing Sheets

U.S. PATENT DOCUMENTS

| | | | |
|---|---|---|---|
| 6,738,053 | B1 | 5/2004 | Borgström et al. |
| 6,839,455 | B2 * | 1/2005 | Kaufman ..................... 382/128 |
| 6,901,277 | B2 * | 5/2005 | Kaufman et al. ............ 600/407 |
| 6,915,265 | B1 | 7/2005 | Johnson |
| 7,065,705 | B1 | 6/2006 | Wang et al. |
| 7,111,230 | B2 | 9/2006 | Euchner et al. |
| 7,120,299 | B2 | 10/2006 | Keskar et al. |
| 7,260,248 | B2 * | 8/2007 | Kaufman et al. ............ 382/128 |
| 2002/0109737 | A1 | 8/2002 | Jaeger |
| 2002/0131625 | A1 | 9/2002 | Vining et al. |
| 2003/0004991 | A1 | 1/2003 | Keskar |
| 2003/0110178 | A1 | 6/2003 | Woods et al. |
| 2004/0049543 | A1 | 3/2004 | Kaminsky et al. |
| 2004/0078215 | A1 * | 4/2004 | Dahlin et al. ................... 705/2 |
| 2004/0205542 | A1 | 10/2004 | Bargeron et al. |
| 2005/0107690 | A1 * | 5/2005 | Soejima ...................... 600/425 |
| 2005/0175245 | A1 | 8/2005 | Sutanto et al. |
| 2006/0061595 | A1 * | 3/2006 | Goede et al. ................ 345/619 |
| 2006/0150079 | A1 | 7/2006 | Albornoz et al. |
| 2007/0022371 | A1 | 1/2007 | Bargeron |

OTHER PUBLICATIONS

Jean-Baptiste Lamy et al.,"An iconic language for the graphical representation of medical concepts," published Apr. 24, 2008, BMC Medical Informatics and Decision Making 2008, 8:16, 12 pages.*

Preiss, B; Kaltenbach, M; Zanazaka, J; Echave, V. Concept graphics: a language for medical knowledge. In: Firsse M. , editor. Proc Annu Symp Comput Appl Med Care. Baltimore, USA: McGraw-Hill; 1992. pp. 515-519.*

Preiss, B; Échavé, V; Preiss, S; Kaltenbach, M. UVAL-MED a universal visual associative language for medicine. Proc Annu Symp Comput Appl Med Care. 1994:262-266.*

H.I. Litt et al.,"Graphic Presentation of Medical Information in the Visual Chart," in Computer-Based Medical Systems, Proc. 1994 IEEE $7^{th}$ Symp. On, pp. 252-257.*

* cited by examiner

MULTI-INPUT REPORTING AND EDITING TOOL

CROSS-REFERENCE TO RELATED APPLICATIONS

The present application claims priority from U.S. Provisional Patent Application No. 60/809,823, filed Jun. 1, 2006, and is a Continuation-in-Part Application of U.S. Nonprovisional patent application Ser. No. 11/176,427, filed Jul. 8, 2005, the contents of both applications which are herein incorporated by reference in their entirety.

BACKGROUND OF THE INVENTION

1. Field of the Invention

The present invention relates to a multi-input reporting and editing method, and system, in which multiple individuals can provide input into creating report content, and provide greater information depth to the report. In particular, the present invention is used in medical applications, such as radiology, and both the input and the output data of the "dynamic" medical reporting and editing method utilizes gesture-, symbol-, or icon-based reporting language which translates into a standardized medical lexicon. The report output is formatted as hierarchical data that can be entered into structured medical databases for the combined purposes of research, education, outcomes analysis, and quality assurance.

2. Detailed Description of the Relevant Art

Medical reporting in its current form is a static process that begins and ends with the initiation of a single text-based report. This can take a number of forms from a consultation, operative/procedure note, history and physical, or imaging test results. Further, the format of the reporting has involved radiologists making notes or marks with wax crayon on x-ray film, or dictating reports into a microphone, which have been nonreproducible, inaccurate, or which take a lengthy time to generate. Regardless of the format and medical findings being described, the author (i.e., physician) issues a text document that is then reviewed by the ordering clinician, who in turn renders a medical management decision based on these report findings.

In reality, however, conventional reported findings are not dynamic, but are static in nature. Accordingly, if the medical report was a dynamic instrument that allowed multiple users' input, and could track follow-up data over time, the report would be more valuable in its ability to guide medical practice management, and create a vehicle for database mining and quality assessment.

Thus, a method and system of medical reporting and editing, which allowed multiple data inputs and end-users to be involved in the accumulation, processing, and analysis of the data elements contained within the report, and which could perform all these tasks in a timely and accurate fashion, and which can combine any of these tasks for efficiency purposes, is desired.

SUMMARY OF THE INVENTION

The present invention relates to a multi-input reporting and editing tool, which performs as a dynamic instrument to allow multiple users' input into creating a report, such that end-users may accumulate, process, and analyze information, in a timely, efficient, and accurate fashion. The multi-input reporting and editing tool allows tracking of follow-up data over time, and creates a vehicle for database mining and quality assessment.

In one embodiment, the present invention is used in medical applications, and utilizes a standardized graphical language (in the form of symbols) that describes informational content associated with the medical findings contained within the report. This standardized symbol language is in turn linked to a standardized lexicon of medical terminology, which is then translated into a hierarchical structured report using symbol-writing recognition software. Once the end-users become familiar with the symbol language, this can in effect be used in lieu of the structured text report. The same informational content can be derived in two different forms by the "reader", who can review report content by simply reviewing the graphical symbol data drawn onto the electronic image or by reading the structured text report.

In one embodiment consistent with the present invention, the symbols of the graphical language are drawn directly onto a high-resolution, touch screen computer monitor using an electronic stylus. The person inputting the graphical language into the medical reporting and editing system, can choose to draw symbols directly onto the computer monitor which displays the medical data (e.g., mammography images) or use a touch screen tablet that is directly integrated with the computer-based medical data.

In either case, the inputted symbols are displayed directly onto the medical data (i.e., images) for the "reader" to review, following report completion. Thus, surgical operative notes, procedure reports (i.e., colonoscopy report), or patient history, or results of a physical examination, all have the same capabilities for receiving the inputted symbols, to allow more than one medical professional involved in the medical care of that individual patient to add to the report. In other words, as the patient passes through a series of events, the various individuals involved in the various steps of data acquisition, processing, interpretation, assimilation, and clinical decision-making, all can input data and findings into the report.

In one embodiment consistent with the present invention, security of the information in the reports can be assured by limiting access to the reports by means of biometric identification systems, for example.

In another embodiment consistent with the present invention, interactive consultation can be performed, with each of the end-users having the ability to "turn on and turn off" the embedded gestures or symbols, such that the combined image/report becomes an electronic consultative tool between the end-users. Thus, the present invention improves on the present methods where users have to move from the images (and the findings contained within them) to the report, which are decoupled and separate from one another.

In another embodiment consistent with the present invention, varying overlays or tiers of reports can be provided, which can show either different findings over time, or different aspects of the findings, thereby providing as much information to the multiple users as possible in one image.

Accordingly, a comprehensive report which provides the capability of integrating multiple data points and different end-user perspectives into a single, all-inclusive electronic document, is achieved. Thus, as the patient's medical care proceeds and additional knowledge is gained, this additional clinical knowledge can be directed back into the original report to clarify (i.e., provide "proof") as to the accuracy of diagnoses. By providing the means to create a dynamic structured medical report, data mining can be performed for the purposes of quality assurance and clinical outcomes analysis.

There has thus been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DETAILED DESCRIPTION OF THE INVENTION

The present invention relates to a multi-input reporting and editing tool, which performs as a dynamic instrument to allow multiple users' input into creating a single electronic, comprehensive report, such that end-users may accumulate, process, and analyze information, in a timely, efficient, and accurate fashion.

In one embodiment consistent with the present invention, the multi-input reporting and editing tool utilizes gesture-based (or symbol-based or icon-based) reporting, which can be provided for any type of image-reporting that would benefit from a "shorthand" that is accurate and descriptive, such as in the fields of medicine (i.e., radiology), landscaping, architecture, etc.

However, the medical (i.e., radiology) application will be the exemplary embodiment as discussed below. In the exemplary radiological application, gesture-based reporting includes a computer-implemented method and computer system, which can be used to create a database of comprehensive gesture-embedded image and text reports from which data mining and other analyses can be conducted.

Figure 1:
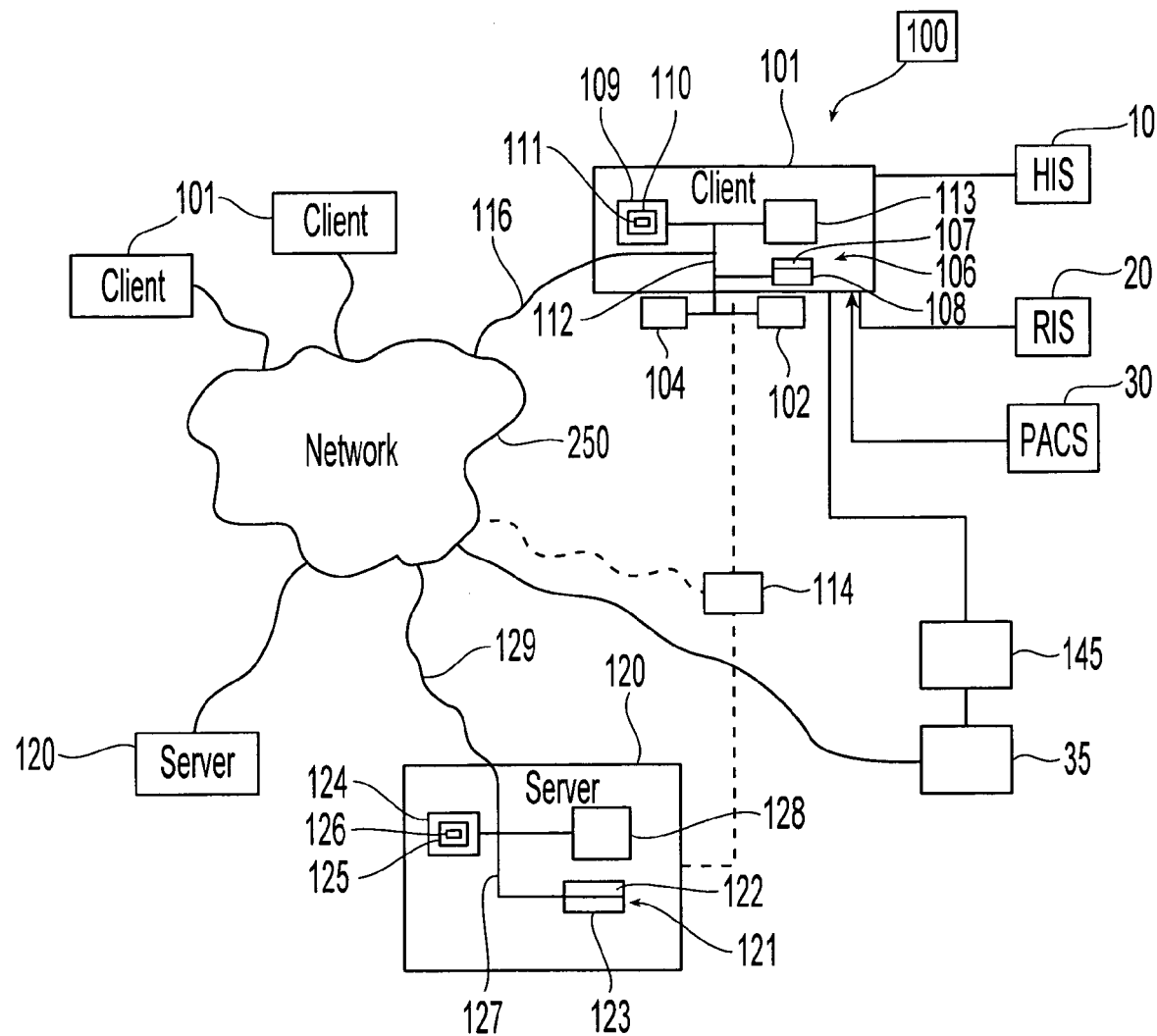
FIG. 1 is a schematic showing the reporting and editing method and system according to one embodiment consistent with the present invention.

In the exemplary embodiment of medical (radiological) applications, the reporting and editing tool or system 100 of the present invention (see FIG. 1) is also designed to interface with existing information systems such as a Hospital Information System (HIS) 10, a Radiology Information System (RIS) 20, a Picture Archiving and Communication System (PACS) 30, and to conform with the relevant standards, such as the Digital Imaging and Communications in Medicine (DICOM) standard, DICOM Structured Reporting (SR) standard, or the Radiological Society of North America's Integrating the Healthcare Enterprise (IHE) initiative.

Thus, bi-directional communication between the reporting and editing system 100 of the present invention and the information systems, such as the HIS 10, RIS 20, and PACS 30, etc., allows the reporting and editing system 100 to retrieve information from these systems and update information therein and provide the desired report generated by the reporting and editing system 100.

Figure 2:
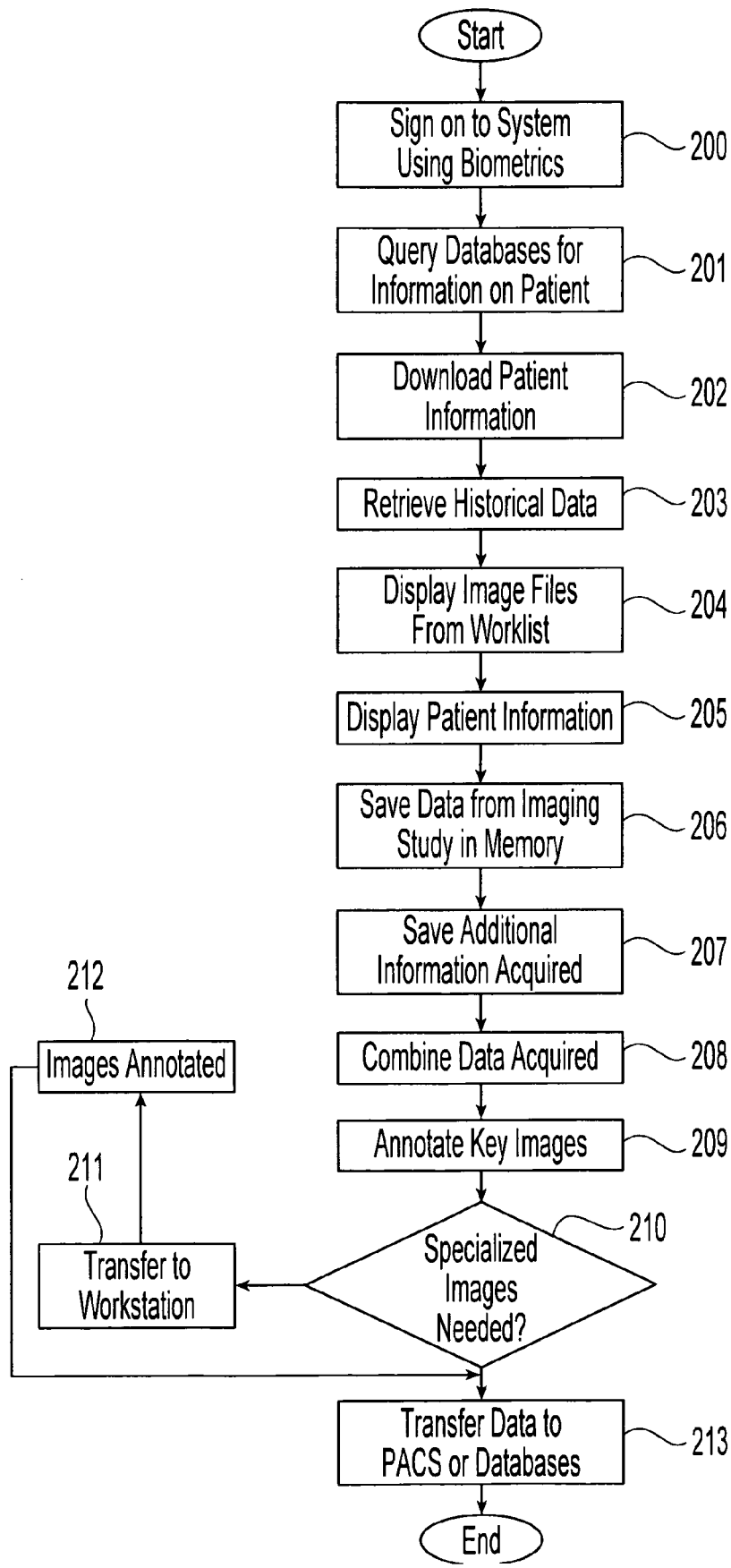
FIG. 2 is a flowchart showing steps in the reporting and editing method according to one embodiment consistent with the present invention.

The reporting and editing system 100 of the present invention (see FIG. 1) includes a client computer 101, such as a PC, which may or not be interfaced or integrated with the PACS 30, and includes an imaging display device 102 capable of providing high resolution of digital images in 2-D or 3-D, for example. However, if the image resolution can be sufficiently high, the client may be a mobile terminal, such as a mobile computing device, or a mobile data organizer (PDA), operated by the user accessing the program remotely from the client (see FIG. 2).

Methods and systems consistent with the present invention are carried out by providing an input means 104 (see FIG. 1), or user selection means, including hot clickable icons etc., or selection buttons, in a menu, dialog box, or a roll-down window of an interface provided at the client 101, and the user may input commands through a programmable stylus, keyboard, mouse, speech processing means, laser pointer, touch screen, or other input means 104.

The input or selection means 104 may be constituted by a dedicated piece of hardware or its functions may be executed by code instructions executed on the client processor 106, involving the display unit 102 for displaying the selection window and a stylus or keyboard for entering a selection, for example.

However, input of the gestures, symbols, or icons, by a user would preferably be accomplished using a multi-functional, programmable stylus 104, which can not only be used to draw symbols onto the image, but can also accomplish other tasks intrinsic to the image display, navigation, interpretation, and reporting processes that are superior to using traditional computer keyboard or mouse methods (both within the PACS and Electronic Medical Report (EMR)). The programmable stylus described in corresponding U.S. Nonprovisional patent application Ser. No. 11/512,199, filed Aug. 30, 2006, is one such tool, and is herein incorporated by reference in its entirety.

The client 101 typically includes a processor 106 as a client data processing means, the processor including a central processing unit (CPU) 107 or parallel processor and an input/output (I/O) interface 108, a memory 109 with a program 110 having a data structure 111, all connected by a bus 112. Further, the client 101 would include an input device or means 104, a display 102, and may also include one or more secondary storage devices 113. The bus 112 may be internal to the client 101 and may include an adapter to a keyboard or input device 104 or may include external connections.

The imaging display device 102 for the present invention is a high resolution touch screen computer monitor, which would allow images, such as x-rays, to be readable and for the gestures or symbols to be applied easily and accurately. Alternatively, the imaging display device 102 can be other touch sensitive devices including tablet, pocket PC, and plasma screens. The touch screen would be pressure sensitive and responsive to the input of the stylus 104 which would be used to draw the gestures or symbols of the present invention, directly onto the image displaying device 102.

In addition, high resolution goggles may be used to provide end users with the ability to review images without the physical constraints of an external computer. For example, a surgeon wearing specialized high resolution goggles to display the cross-sectional radiological image of a brain tumor in 3-D format, would be able to note the gestures on the image highlighting the pathology in question and reporting pertinent characteristics (i.e., anatomic localization, size, etc.), to serve as a guide during surgery. These goggles are used for image-guided surgery and gesture-based reporting would serve to provide consultation on pertinent findings during the course of surgery.

In another example, an internal medicine physician could use these specialized goggles outside the hospital, to review images with embedded gestures or symbols. The images could be downloaded using wireless technology and displayed on the goggles, thereby eliminating the need for a computer screen for image display.

Note that with respect to the client system 101, the graphics user interface is a client application written to run on existing computer operating systems which may be ported to other personal computer (PC) software, personal digital assistants (PDAs), and cell phones, and any other digital device that has a screen or visual component and appropriate storage capability.

The processor 106 at the client 101 may be internal or external thereto, and executes a program 110 adapted to predetermined operations. The processor 106 has access to the memory 109 in which may be stored at least one sequence of code instructions comprising the program 110 and the data structure 111 for performing predetermined operations. The memory 109 and program 110 may be located within the client 101 or external thereto.

Note that at times the system 100 of the present invention is described as performing a certain function. However, one of ordinary skill in the art would know that the program 110 is what is performing the function rather than the entity of the system 100 itself.

The program 110 which runs the reporting and editing method and system 100 of the present invention can include a separate program code for performing a desired operation, or may be a plurality of modules performing sub-operations of an operation, or may be part of a single module of a larger program 110 providing the operation.

The processor 106 may be adapted to access and/or execute a plurality of programs 110 corresponding to a plurality of operations. An operation rendered by the program 110 may be, for example, supporting the user interface, data mining functions, performing e-mail applications, etc.

The data structure 111 may include a plurality of entries, each entry including at least a first storage area that stores the databases or libraries of gesture symbols, or image files, for example.

The storage device 113 stores at least one data file, such as image files, text files, data files, audio, video files, etc., in providing a particular operation. The data storage device as storage means 113, may for example, be a database, including a distributed database connected via a network, for example. The database can be a computer searchable database and may be a relational database. The storage device may be connected to the server 120 and/or the client 101, either directly or through a communication network, such as a LAN or WAN. An internal storage device 113, or an external storage device 114 is optional, and data may also be received via a network and directly processed.

In methods and system consistent with the present invention, the client 101 may be connected to other clients 101 or servers 120, including security (i.e., biometric input means 145), administration, billing or other systems, via a communication link 116 as a client communication means, using a communication end port specified by an address or a port, and the communication link 116 may include a mobile communication link, a switched circuit communication link, or may involve a network of data processing devices such as a LAN, WAN, the Internet, or combinations thereof. In particular, the communication link may be to e-mail systems, fax, telephone, wireless communications systems such as pagers and cell phones, wireless PDA's and other communication systems.

The communication link 116 may be an adapter unit capable to execute various communications protocols in order to establish and maintain communication with the server 120, for example. The communication link 116 may be constituted by a specialized piece of hardware or may be realized by a general CPU executing corresponding program instructions. The communication link 116 may be at least partially included in the processor 106 executing corresponding program instructions.

In one embodiment consistent with the present invention, if a server 120 is used in a non-distributed environment, the server 120 would include a processor 121 having a CPU 122 or parallel processor which is a server data processing means, and an I/O interface 123, but may also be constituted by a distributed CPU 122 including a plurality of individual processors 121 on one or a plurality of machines. The processor 121 of the server 120 may be a general data processing unit, but preferably a data processing unit with large resources (i.e., high processing capabilities and a large memory for storing large amounts of data).

The server 120 also includes a memory 124 with program 125 having a data structure 126 all connected by a bus 127. The bus 127 or similar connection line can also consist of external connections, if the server 120 is constituted by a distributed system. The server processor 121 may have access to a storage device 128 for storing preferably large numbers of programs for providing various operations to the users.

The data structure 126 may include a plurality of entries, each entry including at least a first storage area which stores image files, for example, but may also have alternative embodiments including that associated with other stored information as one of ordinary skill in the art would appreciate.

The server 120 may be a single unit or may be a distributed system of a plurality of servers 120 or data processing units, and may be shared by multiple users in direct or indirect connection to each other. The server 120 performs at least one server program for a desired operation, which is required in serving a request from the client 101.

The communication link 129 from the server 120 is preferably adapted to communicate with a plurality of clients.

The present invention is implemented in software which can be provided in a client and server environment, or in a distributed system over a computerized network across a number of client systems. Thus, in the present invention, a particular operation may be performed either at the client or the server, at the edge of a network or at the center, or both. Therefore, at either the client or the server, or both, corresponding programs for a desired operation/service are available.

In a client-server environment, at least one client and at least one server are each connected to a network 250 such as a Local Area Network (LAN), Wide Area Network (WAN), and/or the Internet, over a communication link 116, 129. Further, even though the systems HIS 10 and MS 20, and PACS 30 (if separate) are shown as directly connected to the client 101, it is known that these systems could be connected to the client over a LAN, WAN, and/or the Internet via communication links. Interaction with users may be through secure and non-secure internet connectivity. Thus, the steps in the methods consistent with the present invention are carried out at the client or at the server, or at both, the server (if used) being accessible by the client over for example, the Internet using a browser application or the like.

The client system 101 may include communications via a wireless service connection. The server system 120 may include communications with network/security features, via a wireless server, which connects to, for example, voice recognition. However, one of ordinary skill in the art would know that other systems may be included.

In another embodiment consistent with the present invention, the client system may be a basic system, and the server may include all of the components necessary to support the software platform of the present invention. Further, the present client-server system may be arranged such that the client system can operate independently of the server system, but that the server system can be optionally connected. In the former situation, additional modules would instead be connected to the client system. In another embodiment consistent with the present invention, the client system and server system can be disposed in one system, rather being separated into two systems.

Although the above physical architecture has been described above as client-side or server-side components, one of ordinary skill in the art would know that the above components of the physical architecture may be in either client or server, or in a distributed environment.

Further, although the above-described features and processing operations may be realized by dedicated hardware, or may be realized as programs including code instructions executed on data processing units, it is further possible that parts of the above sequence of operations are carried out in hardware, whereas other of the above processing operations are carried out using software.

The underlying technology allows for replication to various other sites. Each new site can maintain "state" with its neighbors so that in the event of a catastrophic failure, other server systems can continue to keep the application running, and allow the system to load-balance the application geographically as required.

Further, although aspects of one implementation of the present invention are described as being stored in memory, one of ordinary skill in the art will appreciate that all or part of the methods and systems consistent with the present invention may be stored on or read from other computer-readable media, such as secondary storage devices, like hard disks, floppy disks, CD-ROM, or other forms of ROM or RAM either currently known or later developed. Further, although specific components of the system have been described, one skilled in the art will appreciate that the system suitable for use with the methods and systems consistent with the present invention, may contain additional or different components.

Accordingly, in one embodiment consistent with the present invention, the reporting and editing system 100 and method as used in an exemplary radiology method and system, includes a client computer 101 with image displaying device 102, and an input device 104 which is a programmable stylus. The programmable stylus 104 is used as input means, and can not only be used to draw symbols onto the image, but can also accomplish other tasks intrinsic to the image display, navigation, interpretation, and reporting processes of the present invention.

Thus, in one embodiment consistent with the present invention, the user—in this case the technologist—turns on the client computer system 101, which may be a stand-alone PC, or part of or connected to a client workstation known in the radiological field as the PACS workstation 30. In this exemplary embodiment, the client computer 101 is the PACS 30, and some or all of the present invention, with respect to imaging display device 102, computer memory 109 and program 110 etc., is contained within the PACS 30 instead of being provided separately.

Thus, the technologist logs onto the reporting and editing system 100 once the client 101 is operational.

In one embodiment consistent with the present invention, the technologist signs onto the system 100 utilizing an authentication or identification procedure in step 200 (see FIG. 2), which may utilize biometrics. In this case, a biometrics input means 145 (e.g., facial recognition technology, fingerprint analysis, etc.) is used to identify and authenticate the user (see corresponding U.S. Nonprovisional patent application Ser. No. 11/790,843, filed Apr. 27, 2007, the contents of which are herein incorporated by reference). Specifically, the biometrics technology includes a biometric input means 145 and is connected to the system 100 of the medical enterprise. All information inputted into the biometrics system 35 is recorded in memory or a database 109, 113, 124, 128 etc., which can be accessed by the program 110 such that pertinent information can be retrieved, sorted, and analyzed.

Once authentication and identification takes place, local, regional, and centralized medical databases can be automatically queried by the program in step 201 using the identification-specific electronic signature of the user. All data intrinsic to the medical procedure or examination being performed will be automatically tagged and downloaded into that specific patient's electronic medical database by the program 110 in step 202. At the same time, that patient's medical database is queried by the program 110 in step 203 to provide all historical data relevant to the medical examination or procedure being performed, to assist with planning, protocol, and analysis of the data being collected.

The program 110 will display a menu which will provide a worklist folder listing image files available for analysis, in step 204, and the technologist can then select a particular patient's information, and the program 110 will open up in step 205, and display the patient's records and information.

The technologist will then review the exam-specific data (unique to that patient) that is automatically extracted from information systems (i.e., CPOE, RIS, PACS) by the program 110 in step 203, and confirm the protocol established for the desired examination to be performed on the patient, based on the data in the system 100.

The technologist will then perform the study on the patient as directed, and acquire imaging data based on the pre-selected protocol. The technologist will input and/or save the data from the imaging study in memory 128, etc., of the system 100, in step 206. After data acquisition is completed, the technologist will review the imaging data for completeness and overall quality.

If the imaging data is incomplete, or of poor quality, or there is pathology identified which requires additional data acquisition, the technologist will perform additional image acquisition and store the newly acquired information in the database in step 207.

The technologist will then perform another review of the imaging data, and if complete, will combine the new data with the initial data acquired, to satisfy the examination requirements, in step 208.

The completed imaging dataset will be analyzed by the technologist, and "key images" identified for annotation. In one embodiment, the technologist will insert the annotations using gesture-based reporting symbols in step 209, although one of ordinary skill in the art would know that other types of annotations, including text, may also be used.

The gesture-based reporting (GBR) symbols would correspond to the predefined terms for a particular type of pathology. The annotations would be made to highlight areas of suspected pathology, to make a quantitative analysis of each of the images (i.e., linear and density measurements), a qualitative analysis of the image (i.e., temporal change from comparison studies stored in the database), and quality assurance limitations (i.e., motion artifacts).

After imaging review and annotation are completed by the technologist, the technologist may make a determination as to whether specialized image processing is required in step 210. If additional image processing is required, the technologist may so order, and the imaging dataset would be transferred to the workstation 101 by the program 110 in step 211. The image processing/reconstructions would be performed by a specialist, who would insert annotations using GBR symbols, onto the images in step 212. The completed imaging dataset (with annotations) would be then transferred to the PACS 30 for interpretation by the radiologist, in step 213.

Figure 3:
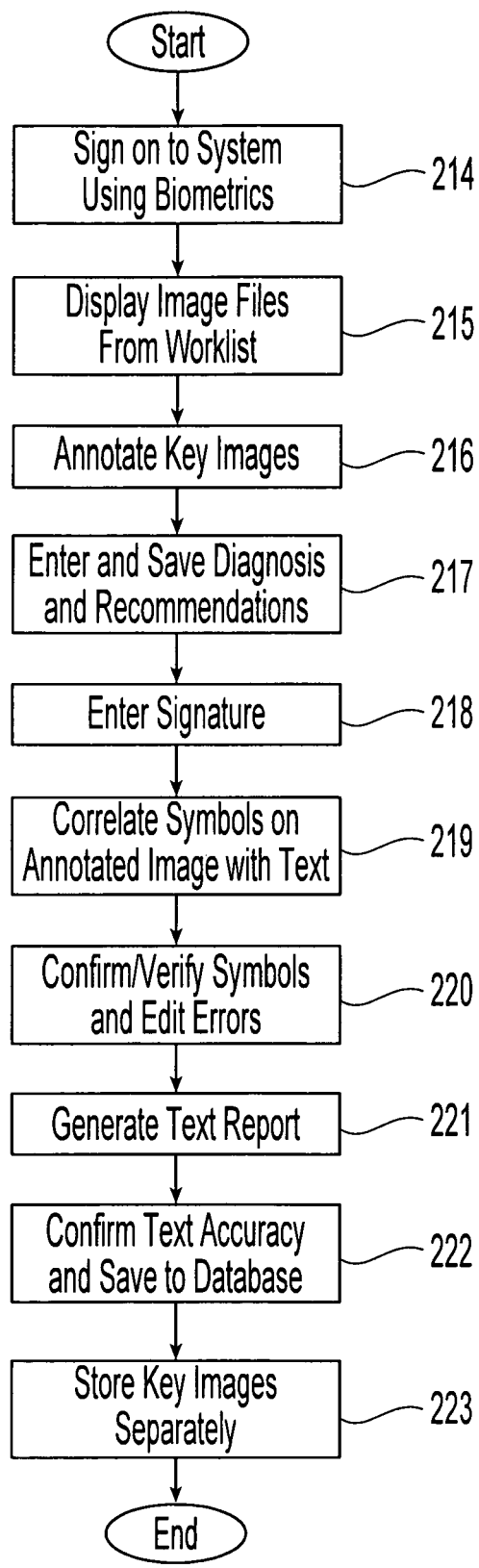
FIG. 3 is another flowchart showing steps in the reporting and editing method according to one embodiment consistent with the present invention.

The radiologist would sign into the PACS 30 using the biometrics identification and authentication procedure in step 214 (see FIG. 3), and retrieve the image dataset stored on the patient, from the PACS database (Unread Worklist) in step 215 (see FIG. 3).

Note that in one embodiment, the image dataset may be presented in both a GBR "On" or GBR "Off" format. For example, the program 110 can provide the user the option of viewing all annotations made by previous users—for example, in different colors or another format—so that the user may recognize the information inputted by the different users. However, if the user wishes to review the images without the annotations of other parties, the user may turn the GBR "Off", and the image dataset will be provided without any annotations.

Assuming the GBR is "On", the radiologist would review the images with the annotations made by the technologist, on the PACS workstation 30. The radiologist will make his/her own GBR annotations on "key images" in his/her review process, the "key images" which are saved to the PACS database in step 216. The radiologist's annotations would be made in a different color or format from the technologist's annotations, to distinguish them from each other.

Further, in one embodiment, the radiologist will also be able to perform an editing function—to make additions or deletions in GBR to the annotations found in the image dataset. The editing function is awarded to the user based on the privileges the user has been authorized, according to predetermined criteria set by the program 110.

In one embodiment, if the radiologist is correlating with a historical comparison study and notices some previously reported findings remain, he/she can pull up a previous image, then either redraw the appropriate gestures, symbols, or annotations, or re-propagate gestures, symbols, or annotations from the prior study by dragging them over to the new study using the (programmable) stylus 104. Thus, the program 110 will allow the movement of gestures, symbols, or annotations from one image to another, in a similar fashion to a "copy" or "cut and paste" function in word processing.

In another embodiment, to facilitate the interpretation process, the radiologist can utilize automated decision support by clicking on the corresponding icon with the (programmable) stylus 104. Examples of automated decision support include temporal subtraction (where changes over time are noted), computer-aided detection (CAD) (which detects pre-defined pathologies), computer-generated measurements and differential diagnosis (which provides a list of potential pathologies depending on the radiological findings). These automated decision support systems can provide findings which can be recorded onto the image in annotations or in GBR, by the radiologist, or automatically translated into gestures or annotations, depending on how the automated decision support system works and can be integrated into the reporting and editing method and system of the present invention.

Thus, the radiologist's annotations will highlight the areas of pathology in the images using GBR, for example, for modifiers such as anatomic location, temporal change, and clinical significance. The radiologist will also make a diagnosis (differential or specific), and make follow-up recommendations, which will be saved in the system 100 as step 217. The follow-up recommendations will include descriptors such as degree of certainty, measurements (i.e., size), morphology, and number.

After completion of image review, interpretation, and diagnosis, the radiologist may then sign the annotated image by electronically placing his/her initials (using the stylus 104) on the image, in step 218.

After saving the annotated images, the program 110 will correlate the gesture or modifier recorded on the image, to a database 113, 114 or 128 for example, of gestures which provide the text for the correlation of the gesture or modifier, in step 219. The program 110 may then provide confirmation and verification of the gestures or modifiers to be saved, in step 220, and provide for editing of the text and/or the gesture or symbol for the image and the corresponding report related to that gesture in the event of an error. The radiologist would then re-enter the annotation, and repeat the process, eventually confirming the gesture or annotation when visualizing the correct corresponding text. The program 110 will confirm the text as correct, and then save the annotated image.

After the GBR symbols are saved and correlated, the GBR symbols are transcribed into a structured text report according to a predefined format in step 221. The radiologist will confirm the structured text report or combined symbol/text report to ensure that it is accurate and complete in step 222.

In generating a report using the reporting and editing system, digital ink technology (i.e., electronically creating symbols and translating them into text) and specialized recognition software to translate the gestures or symbols used to map to specific radiological findings and concepts into an itemized text report, would be provided. The program 110 containing this recognition and report generation software is provided in the program 110 and in one embodiment consistent with the present invention, possibly integrated with the PACS 30 which is responsible for image display, distribution, and storage (of both medical images and reports). Natural language processing (NLP) would provide the intelligence to convert the gestures and itemized text into a standard prose format.

In one embodiment, more than one radiologist can participate in the reporting process. These situations include: 1) academic practices, where a radiologist in training (i.e., radiology resident) renders a "preliminary" interpretation, which is in turn followed by an attending radiologist "final" interpretation; 2) radiologist subspecialty consultation, which can be requested by the radiologist rendering initial interpretation; and 3) expert "second" opinion, at the request of either the referring clinician or patient.

Thus, the radiologist's findings can be correlated with those of a second reader or radiologist, and the second radiologist's GBR symbols may be displayed on the monitor using a separate schema from the "primary" reader symbols (i.e., different color etc.). Any discordant symbols would be presented to the radiologist of record for action—in one embodiment, through a visual display where the discordant symbols "blink" in order to acquire attention or are uniquely color coded.

In these situations, the sequential radiologist's annotations and/or edits are electronically tracked and recorded by the GBR editing/auditing tool for quality assurance analysis. As with the technologists, each individual reader or radiologist would have a special code (e.g., different color) assigned to their GBR annotations, thereby allowing anyone reviewing the annotated images to differentiate one user's GBR annotations from another. As stated above, each individual reader's annotations can be selectively turned "on" or "off" by the other users during review.

The "saved" annotated "key images" may be stored separately in the database or archive 113, 114 or 128, for example, in addition to the comprehensive imaging dataset. These "key images" with the embedded symbols, may also be electronically sent directly to the referring clinician (based on a predefined communication protocol, such as e-mail, etc.) in step 223.

Figure 4:
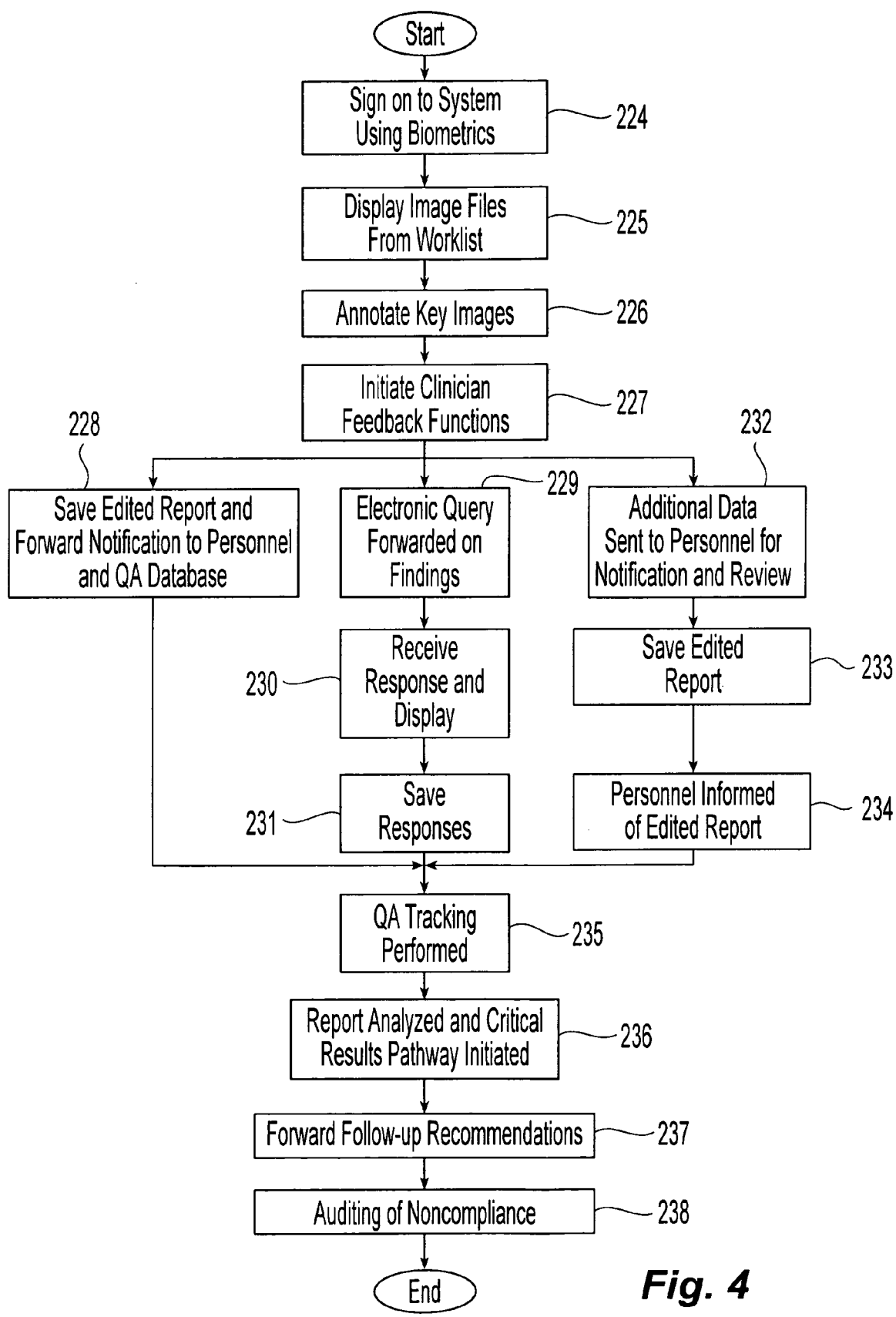
FIG. 4 is yet another flowchart showing steps in the reporting and editing method according to one embodiment consistent with the present invention.

In one embodiment, the clinician signs onto the PACS 30 for review of the examination results, in step 224 (see FIG. 4), using the biometrics identification and authentication procedure, and retrieves the image dataset stored on the patient, from the PACS database (i.e., Worklist) in step 225.

The clinician may then review the imaging exam and GBR report. If the GBR is turned "On", the physician can select which report functions to review—such as the technologist, radiologist attending, and perhaps the radiologist resident or a consultant. If the GBR is turned "Off", the clinician can review the imaging data with GBR mark-up.

The clinician may then elect to insert their own annotations representing their findings, using GBR symbols, for example (i.e., specifically color coded to that clinician), in step 226.

In one embodiment, in step 227, the clinician can elect one of three "clinician feedback" functions into the GBR schema: 1) report editing (i.e., modifying GBR findings displayed on the "final" radiologist report); 2) consultation (i.e., query which asks for additional clarification of a reported finding); and 3) additional information (i.e., additional clinical data supplied to the radiologist to assist with exam interpretation).

Specifically, in the report editing feedback function, if the clinician's GBR findings are different from the "final" radiology report (e.g. new, deleted, or modified), an electronic notification is sent to report database 124, 128 etc. by the program 110 in step 228. This notification will also be made by the program 110 in step 228, to the radiologist of record, to the patient, and to the quality assurance (QA) database.

In the consultation function, the clinician can also generate an electronic query (i.e., consultation) to the interpreting radiologist, relative to one of the reported findings. To generate this query, in step 229, the clinician enters a query symbol (i.e., "?") attached to the GBR symbol in question with corresponding text. The radiologist is then sent electronic notification of the query by the program 110, and the program 110 will solicit a response via electronic means (i.e., e-mail, fax, etc.). The radiologist's response will be received and displayed for the clinician by the program 110 in step 230, and saved in the database in step 231. All communications between any of the users are stored within the GBR report database 124, 128, etc. using the program 110 of the GBR auditing/editing tool of the present invention. The auditing function may be similar to that disclosed in copending U.S. patent application Ser. No. 11/586,580, filed Oct. 26, 2006, the contents of which are herein incorporated by reference in its entirety.

In another embodiment, in the information request function, the clinician may enter an additional information symbol (e.g., "I") attached to a specific GBR symbol or to the report as a whole, and the program 110 will notify the radiologist, for example, of the additional report input, by electronic means (i.e., e-mail, fax etc.) in step 232. Upon review of the additional report, the radiologist may elect to edit the original report based on the additional clinical information received, and the re-edited report will be saved in the system 100 in step 233, and the clinician notified by the program 110 by electronic means in step 234.

As with all editing functions, the data inputted and edited in the report database 124, 128 etc., is tracked for quality assurance purposes by the program 110 in step 235.

The quality assurance pathways are outlined in greater detail in the Quality Assurance Scorecards applications, U.S. patent application Ser. No. 11/699,348, filed Jan. 30, 2007, U.S. patent application Ser. No. 11/699,349, filed Jan. 30, 2007, U.S. patent application Ser. No. 11/699,350, filed Jan. 30, 2007, U.S. patent application Ser. No. 11/699,344, filed Jan. 30, 2007, and U.S. patent application Ser. No. 11/699/351, filed Jan. 30, 2007, and in the quality assurance in radiology application, U.S. patent application Ser. No. 11/412,884, filed Apr. 28, 2006, the contents of all of which are herein incorporated by reference in their entirety.

When the report is finalized and saved in the database 128 etc., it is normally saved in one of two formats: 1) as a GBR symbol set, or 2) a hierarchical structured text report. However, a mixture of both formats may be saved by the program 110 depending on the guidelines set in the system 100. If an emergent finding is recorded, an electronic "critical results" pathway is automatically initiated by the program 110 to document delivery and receipt by the referring clinician, according to the auditing and/or QA scorecard methods in step 236.

If a follow-up recommendation is recorded in the database 124, 128 etc. as being ordered by the clinician, a computerized intelligent agent of the program 110 ensures notification and compliance for the follow-up recommendation in step 237. For example, if the follow-up consists of an imaging study (e.g., MRI), the electronic order is sent by the program 110 to the referring clinician, and the program 110 may simultaneously order and schedule the recommended exam.

Further, if a follow-up procedure is recommended (e.g., biopsy or surgery), an electronic notification is sent by the program 110 to the patient's EMR with "high priority" status that tracks receipt by the referring clinician according to the program's 110 auditing function. If the recommended follow-up is not documented within the system 100 in a defined time period, notification is automatically sent by the program 110 to the QA database 124, 128 etc, for automatic review by a designated compliance officer in step 238. Further, other auditing and quality assurance functions, for example as described in the above-noted corresponding patent applications, may be used.

The program 110 will record the reports in the report database, to include the following GBR data elements: identity of author; date and time of GBR or annotated entry; specific GBR symbols recorded (mapped to standardized lexicon);

edited symbols (GBR symbols recorded in "preliminary" reports not contained within "final" report); frequency distribution of GBR or annotated modifiers and descriptors (by authors); record of clinician or subspecialty consultations; and clinical outcomes analysis (diagnostic accuracy of GBR/text reports relative to clinical data (i.e., discharge summary, pathology report)). The program 110 will automatically send the GBR and/or text report analyses to all authoring technologists, radiologists, and clinicians (along with individual and collective summary statistics), by electronic means (i.e., e-mail, fax etc.).

As stated previously, in addition to the reports being comprised of input from end-users, computer-derived data can be integrated into the report analysis by including specialized computer-assisted diagnosis (CAD) software and data derived from the electronic medical record (EMR), pertinent to the presumptive diagnosis.

In another embodiment consistent with the present invention, varying overlays or tiers of reports can be provided, which can show either different findings over time, or different aspects of the findings, thereby providing as much information to the multiple users as possible in one image.

The comprehensive report thus compiled, provides the capability of integrating these multiple data points and different end-user perspectives into a single, all-inclusive electronic document. As the patient's medical care proceeds and additional knowledge is gained, this additional clinical knowledge can be directed back into the original report to clarify (i.e., provide "proof") as to the accuracy of diagnoses. By providing the means to create a dynamic structured medical report, data mining can be performed for the purposes of quality assurance and clinical outcomes analysis.

In one embodiment consistent with the present invention, security of the information in the reports can be assured by limiting access to the reports by means of biometric identification systems described in a corresponding application, for example.

In addition, two additional report databases can be accessed for educational review and training: 1) an educational database and teaching files report database, which contains cases of educational interest which can be automatically tagged by the program 110 by the technologist, radiologist, or clinician authors; and 2) a QA database, which contains cases of identified QA deficiency, as identified by the technologist, radiologist, or clinician authors.

In both cases the program 110 will perform data mining to compile these databases, and present them to the user at predetermined times. In particular, the QA database will operate in accordance with the methods described in the corresponding QA scorecards applications.

In one example consistent with the present invention, a technologist is scheduled to perform a renal ultrasound examination on a patient with the clinical history of hematuria. After undergoing biometrics identification and authentication of the patient, technologist, and any other personnel, according to identification/authentication procedures specified in the corresponding biometrics patent application, the program 110 will provide information on the patient and the procedure for the technologist to confirm. Once confirmed, the technologist may proceed with the examination.

During the examination, the technologist (sonographer) identifies a solid mass arising from the left kidney which he/she believes is worrisome for a renal malignancy. The technologist identifies the image obtained as a "key image" and annotates the image with the GBR symbols for mass, along with pertinent size measurements and the presumptive diagnosis of "malignancy". The program 110 saves this image in the database 124, 128 etc., and may save the key image in a "key image" database.

The technologist may find an additional "key image", which he/she highlights and annotates directly on the computer monitor 104 or hand-held tablet etc., to indicate a second mass in the contralateral right kidney. The technologist will use the GBR symbols for mass, uncertain clinical significance, and corresponding size measurements in the annotation.

When the radiologist is reviewing the ultrasound dataset with technologist GBR findings, he/she may use the editing function which will allow for the technologist's reported findings to be directly modified by the radiologist, in his/her final report. The radiologist may agree with the reported findings of left renal mass (malignancy), and may elect to add a few additional modifiers including "biopsy recommended" and "high clinical significance" directly into the report using annotations. The radiologist may then determine that the technologist's findings for the right renal mass are erroneous and may replace the annotated findings with annotations indicating a 3.5 cm cyst, of benign etiology directly in the same report.

The program 110 of the reporting and editing tool of the present invention functions to record the individual findings of each reader/user along with the sequential changes made by each user. Each modification of the annotated report is saved in the database 124, 128, and in the QA database etc. The final report findings of "malignant left renal mass" and "biopsy recommended" by the radiologist, initiates the "critical results pathway" where the program 110 electronically notifies the referring clinician and documents receipt of his/her confirmation. The intelligent agent of the program 110 will query the patient's EMR folder and link pathology findings to the original ultrasound report, once the biopsy has been completed. This information is also recorded by the program 110 into the report database for future analysis, with feedback automatically sent by the program 110 to both the technologist and radiologist authors.

In a second exemplary scenario, a patient is scheduled to undergo a screening mammogram for breast cancer. The technologist will undergo a biometric identification/authentication, as well as the patient, as required. After image acquisition has been completed by the technologist, the technologist (mammographer) may identify an area of suspicious calcifications at the 2 o'clock position of the right breast. The technologist may annotate the "key image" and may elect to perform additional spot magnification views of the right breast for improved characterization of the indeterminate calcifications. After reviewing these additional magnification views, the technologist may annotate the additional images and record the following findings, in one embodiment using the GBR symbols and text: microcalcifications, right breast, 2 o'clock position, suspicious for malignancy. The technologist may also identify this particular exam as a "clinical high priority", where the program 110 automatically directs the exam to the top of the unread mammography queue.

The radiologist is then electronically alerted by the program 110 of the "priority status" and may display the exam immediately for the user. While the current exam images are displayed by the program 110, recent historical comparison studies from 1 and 3 years earlier are retrieved from the database 114, 128 etc. by the program 110, and displayed alongside the current exam. The historic comparison exam from 3 years earlier was interpreted at a time when annotated images, such as GBR annotations, were not in use, so the radiologist must manually review the free text report and unmarked images displayed by the program 110. The comparison study from 1 year earlier did have GBR reporting and as a result, has the historical symbols auto-populated onto the current study by the program 110.

The radiologist sees that no microcalcifications were reported at the 2 o'clock position from one year earlier, however, in retrospect, they were present but of lesser conspicuity. When the CAD software program is applied (i.e. "turned on") by the program 110, three findings are identified by the radiologist, including a right axillary mass and calcifications at the 2 and 6 o'clock positions of the right breast. The radiologist then may edit three different GBR symbols for his/her final report which may include the technologist's findings, the prior year findings (which were auto-populated onto the current study by the program 110), and the CAD findings. All edited functions are recorded and entered into the report database 114, 128 etc. by the program 110.

These final findings and edits may include the following: 1) agreement on the technologist's findings of malignant microcalcifications: right breast, 2 o'clock position; 2) added findings of: a) "surgical consultation and biopsy" recommended; b) marked interval increase compared to prior study; and c) high clinical significance; and 3) edited CAD findings for the right axillary mass and 6 o'clock calcifications: a) lymph node, right axilla, not significant; and b) calcifications, right breast, stable, benign. The findings initiate the "critical results" reporting pathway by the program 110 with all subsequent data (including pathology) recorded in the report database 124, 128 etc., and sent to the technologist and radiologist for review.

In a third exemplary scenario related to a colonoscopy, a gastroenterologist is consulted by an internist for a patient found to have a 3 cm polypoid lesion within the cecum on an earlier abdominal CT. The gastroenterologist elects to perform a colonoscopy for further evaluation along with biopsy. After the patient and the relevant personnel are identified and approved by the system for performing the procedure (using biometrics in one embodiment), the colonoscopy is performed.

During the course of the colonoscopy the gastroenterologist identifies three lesions within the colon at the following locations: 1) 3.7 cm infiltrative mass cecum (corresponding to the CT abnormality); 2) 1.0 cm pedunculated polyp in sigmoid colon; 3) 1.5 cam sessile polyp in mid transverse colon. The gastroenterologist then decides to biopsy the cecal and mid-transverse colon lesions. In the procedure note, the gastroenterologist describes the number, size, morphology, and anatomic locations of each lesion using GBR symbol language, for example, over a standard colon template. The gastroenterologist also links the original CT report to his/her GBR-procedure note using the programmable stylus 104, for example, and edits the CT findings by adding the findings for the 2 additional (sigmoid and mid-transverse colon) findings not originally reported. These edits are automatically saved and sent by the program 110 to the radiologist interpreting the original CT report, along with photographs obtained during the colonoscopy procedure.

When the pathology report is received, the biopsy data is automatically tagged by the program 110 to both the original CT and subsequent colonoscopy reports and sent by the program 110 to the authoring physicians. All edited data is recorded in the EMR and PACS databases 30, 128 etc., for example, and results tabulated into each respective report database 30, 128, etc., by the program 110.

In a fourth exemplary scenario, a cardiology consultation is requested by an orthopedic surgeon prior to an elective knee arthroplasty. After patient intake, using biometrics, for example, the patient is initially seen by the cardiology Fellow in training, who issues a consultation report using GBR, for example, that incorporates the clinical exam, EKG, and echocardiography findings into a report that is saved by the program 110 in the database 124, 128 etc. Based on the cardiology Fellow's assessment, the patient is low risk for heart disease and "cleared" for surgery.

The patient is subsequently evaluated by the attending cardiologist and is thought to be at "high risk" for coronary artery disease (based on abnormalities in the EKG and clinical exam not appreciated by the Fellow). The final cardiology consultation records saved by the program 110, include both the findings of the cardiology Fellow and attending physicians, with incorporated annotated "key images" from the EKG and echocardiography exams (each of which contains annotated or GBR findings, for example, from the technologists performing those exams).

The "final" consultation report saved by the program 110 will contain all of the above data, which have been edited by the attending cardiologist with his/her final interpretation. The attending cardiologist may determine that this case is an excellent teaching study (based on divergent opinions) and will instruct the program 110 to electronically send the data on this case to the Electronic Educational Database (EED), so it can be used for future education and training. The EED database will provide future residents and fellows with the ability to track all reported findings from each end-user perspective (i.e., EKG technician, echocardiology sonographer, and cardiology fellow etc.) along with the final report findings of the cardiologist.

The reporting and editing method and system of the present invention provides the means by which medical imaging data and corresponding reports can remain "coupled" and not segregated, as is the current practice. In addition to providing the end-users with a fast and reliable means to simultaneously review findings and results, it also provides a unique means with which sequential data can be recorded and tracked throughout the various phases of the medical imaging cycle (i.e., acquisition, review, interpretation and clinical feedback). Unlike existing reporting systems which do not record observational data from multiple participants, the present invention provides a tool for multi-practitioner input (i.e., technologists, radiologists, consultants, and clinicians) along with a reliable method to identify, track, and analyze these various inputs. By utilizing a standardized lexicon and downloading all this structured data into a mineable database, statistical analyses can be performed with educational feedback to facilitate improved diagnosis and clinical outcomes.

In addition, the present invention is compatible with the use of biometrics to identify and authenticate patients and practitioners in medical enterprises, with gesture-based reporting methods and systems, the use of a programmable stylus to navigate and perform editing and display functions in medical applications, and the use of QA scorecards to perform auditing and quality assurance functions in medical applications. Collectively, these compatible methods and systems provide a means by which patient-specific, medical data can be authenticated, extracted, and cross-referenced from multiple information systems (CPOE, RIS, PACS, EMR) to maximize the efficiency and accuracy of medical imaging.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented medical reporting and editing method comprising:
displaying a stored image for a user on a display, said stored image containing of a plurality of annotation symbols embedded within said image and corresponding to a pre-defined, standardized graphical language that describes informational content associated with medical findings, wherein said graphical language is predetermined and said informational content is not displayed on said image;
displaying a current image for the user on said display with said stored image; and
autopopulating, upon receipt of a command, said current image with said plurality of embedded annotation symbols corresponding to the standardized graphical language, from said stored image, said embedded annotation symbols from said stored image being distinguished from those of said current image by color or format.

2. A computer-implemented medical reporting and editing method comprising:
displaying a first image to a user for review;
displaying a second image to said user on a same display as said first image, said second image which includes at least one annotated symbol embedded within said second image and corresponding to a pre-defined, graphical language that describes informational content associated with medical findings, wherein said graphical language is predetermined and said informational content is not displayed on said image;
moving said at least one annotated symbol from said second image onto said first image on said display, using an input device;
receiving said at least one annotated symbol from said second image on said first image, and embedding said annotated symbol within said first image, thereby producing an updated annotated first image; and
storing said updated annotated first image with said at least one annotated symbol thereon in a database.

3. A computer-implemented medical reporting and editing method comprising:
displaying an image for a first user;
receiving and embedding a first annotation within said image, said first annotation input by said first user using an input device and including at least one of a plurality of symbols corresponding to a pre-defined, standardized graphical language that describes informational content associated with medical findings, wherein said graphical language is predetermined and said informational content is not displayed on said image;
storing said annotated image annotated by said first user with said at least one symbol thereon in a database;
displaying said annotated image annotated by said first user, to a second user;
receiving and embedding a second annotation within said image, said second annotation input by said second user using another input device, and including at least one of a plurality of additional symbols corresponding to additional information utilizing the standardized graphical language, thereby automatically producing an updated annotated image; and
applying automated medical decision support systems to interpret said symbols in said updated annotated image, and to automatically generate a report therefrom.

4. A computer-implemented reporting and editing method comprising:
displaying an image for a first user on a computer monitor;
receiving a first annotation on said image, said first annotation input by said first user and including at least one of a plurality of symbols corresponding to predetermined information;
storing said annotated image with said at least one symbols thereon;
displaying said annotated image to a second user;
receiving a second annotation on said image, said second annotation input by said second user and including at least one of a plurality of additional symbols corresponding to additional predetermined information, thereby producing an updated annotated image;
wherein said symbols annotated by said first user are distinguished in at least color or format by said symbols annotated by said second user; and
automatically comparing said symbols annotated by one of said first or said second users, to a database of said plurality of symbols, such that when said symbols annotated by one of said first or said second users are not recognized and are discordant symbols, said first or said second users are automatically notified of said discordant symbols by a visual notification system on said computer monitor.

5. A computer-implemented medical reporting and editing method comprising:
displaying an image for a first user;
receiving and embedding a first annotation within said image, said first annotation input by said first user using an input device and including at least one of a plurality of symbols corresponding to predetermined information, thereby producing an annotated image, each symbol of said plurality of symbols being a pre-defined, graphical language that describes informational content associated with medical findings, wherein said graphical language is predetermined and said informational content is not displayed on said image;
storing said annotated image annotated by said first user with said at least one symbol thereon in a database;
displaying said annotated image annotated by said first user, to a second user;
receiving and embedding a second annotation within said image, said second annotation input by said second user using another input device, and including at least one of a plurality of additional symbols corresponding to additional predetermined information, thereby producing an updated annotated image, wherein said symbols annotated by said first user are distinguished in at least color or format by said symbols annotated by said second user to show said annotations inputted by said first user or said second user;
allowing edits to be made to at least one of said first or said second annotations on said updated annotated image by at least one of said first or said second users based on a predetermined access granted to said at least one of said first or said second users;
automatically correlating the graphical symbols into a standardized lexicon of medical terminology that converts to one of a graphical medical report or a textual medical report in said database; and
automatically updating said medical report to be stored in said database, by dynamically changing its contents over time whenever each said updated annotated image is created.

6. The method according to claim 5, wherein said first and second annotations are performed over time on a plurality of images.

7. The method according to claim 5, wherein an input device is used to annotate said image or said updated annotated image with said symbols by said first user and said second user.

8. The method according to claim 7, wherein said input device is a programmable stylus.

9. The method according to claim 7, further comprising: applying automated decision support systems to interpret said updated annotated image.

10. The method according to claim 9, wherein findings from said automated decision support systems can be shown on said updated annotated image as at least one of text or symbols, wherein said symbols from said automated decision support systems differ in at least one of a format and a color from said symbols inputted by said first or said second users.

11. The method according to claim 10, wherein neural networks are applied to further define and interpret said updated annotated image.

12. The method according to claim 9, wherein said report contains both said text and said symbols.

13. The method according to claim 7, wherein said updated annotated image with symbols thereon is stored separately as a key image from other images in said image study.

14. The method according to claim 13, wherein said key image is displayed in a pre-selected user format, which includes pre-selected variables.

15. The method according to claim 7, further comprising: providing additional data to a user to assist in image interpretation of said updated annotated image.

16. The method according to claim 5, further comprising: providing said image from a plurality of images in an image study.

17. The method according to claim 5, further comprising: confirming said text correctly denotes said symbols when said symbols are placed on said image by said first or said second users; and editing said text when said symbols are incorrectly denoted.

18. The method according to claim 5, wherein the method is used in the field of radiology.

19. The method according to claim 5, wherein temporal subtraction can be applied to said reports to show changes in said updated annotated image.

20. The method according to claim 5, wherein said updated annotated image includes one of an x-ray, a digital representation, a photograph, a graphical representation, a blueprint, or a medical printout.

21. The method according to claim 5, wherein said displaying steps are performed by a Picture Archiving and Communication System (PACS).

22. The method according to claim 5, wherein said storing step is performed by a Picture Archiving and Communication System (PACS).

23. The method according to claim 5, further comprising: receiving an additional annotation of at least an additional symbol from said plurality of symbols, wherein said additional symbol corresponds to a modifier, which identifies and quantifies said updated annotated image.

24. The method according to claim 5, wherein said display is one of a touch screen or a pair of goggles.

25. The method according to claim 5, further comprising: utilizing biometrics to identify and authenticate said first or second users;
wherein said predetermined access granted to said first or second users includes differing log in and edit privileges of said updated annotated image and report based on predetermined criteria.

26. A computer system having a program for performing medical image reporting and editing, comprising:
means for displaying an image;
means for receiving and embedding an annotated image with at least one of a plurality of symbols corresponding to predetermined information, to produce an updated annotated image, each symbol of said plurality of symbols being a pre-defined, graphical language that describes informational content associated with medical findings, where said graphical language is predetermined and said informational content is not displayed on said image;
wherein said symbols are distinguished in at least color or format from other of said plurality of symbols added by different users and/or at different times;
means for storing said updated annotated image by each said user, with said symbols thereon;
means for allowing edits by each said user, to be made to at least one of said first or second annotations on said updated annotated image based on a predetermined access granted to the users;
means for correlating the graphical symbols into a standardized lexicon of medical terminology that converts to one of a graphical medical report or a textual medical report to be stored in said database; and
means for automatically updating said medical report in said database, by dynamically changing its contents over time whenever each said updated annotated image is created.

27. The computer system of claim 26, further comprising:
means for forwarding said updated annotated image to a selected user.

28. The computer system according to claim 26, further comprising:
means for applying automated decision support systems to interpret said updated annotated image.

29. The computer system according to claim 28, further comprising:
means for providing additional data to a user to assist in image interpretation of said updated annotated image.

30. The computer system according to claim 26, further comprising:
means for confirming said text correctly denotes said symbols when said symbols are placed on said updated annotated image; and
means for editing said text when said symbols are incorrectly denoted.

31. The computer system according to claim 26, further comprising:
means for receiving an additional annotation of at least an additional symbol from said plurality of symbols, wherein said additional symbol corresponds to a modifier, which identifies and quantifies said updated annotated image.

32. A computer system for performing medical image reporting and editing, comprising:
at least one memory containing at least one program comprising the steps of:
displaying an image for a first user;
receiving and embedding a first annotation within said image inputted by said first user using an input device, of at least one of a plurality of symbols corresponding to predetermined information, each symbol of said plurality of symbols being a pre-defined, graphical language that describes informational content associated with medical findings, wherein said graphical language is predetermined and said informational content is not displayed on said image;

storing said annotated image annotated by said first user with said symbols thereon in a database;

displaying said annotated image annotated by said first user, to a second user;

receiving and embedding a second annotation within said image inputted by said second user using another input device, of at least one of a plurality of additional symbols corresponding to predetermined information, thereby producing an updated image, wherein said symbols annotated by said first user are distinguished in at least color or format by said symbols annotated by said second user to show said annotations inputted by said first user or said second user;

allowing edits to be made to at least one of said first or said second annotations on each of said updated annotated images by at least one of said first or said second users based on a predetermined access granted to said at least one of said first or said second users;

automatically correlating the graphical symbols into a standardized lexicon of medical terminology that converts to one of a graphical medical report or a textual medical report in said database; and automatically updating said medical report in said database, by dynamically changing its contents over time whenever each said updated annotated image is created; and at least one processor for running the program.

33. A computer-readable medium whose contents cause a computer system to perform medical image reporting and editing, the computer system having a program comprising the steps of:

displaying an image for a first user;

receiving and embedding a first annotation within said image inputted by said first user, of at least one of a plurality of symbols corresponding to predetermined information, each symbol of said plurality of symbols being a pre-defined, graphical language that describes informational content associated with medical findings, wherein said graphical language is predetermined and said informational content is not displayed on said image;

storing said annotated image annotated by said first user with said symbols thereon in a database;

displaying said annotated image annotated by said first user, to a second user;

receiving and embedding a second annotation within said image inputted by said second user using another input device, of at least one of a plurality of additional symbols corresponding to predetermined information, thereby producing an updated image, wherein said symbols annotated by said first user are distinguished in at least color or format by said symbols annotated by said second user to show said annotations inputted by said first user or said second user;

allowing edits to be made to at least one of said first or said second annotations on each of said updated annotated images by at least one of said first or said second users based on a predetermined access granted to said at least one of said first or said second users;

automatically correlating the graphical symbols into a standardized lexicon of medical terminology that converts to one of a graphical medical report or a textual medical report in said database; and automatically updating said medical report in said database, by dynamically changing its contents over time whenever each said updated annotated image is created.

34. A computer-implemented medical reporting and editing method comprising:

displaying an image for a first user;

receiving and embedding a first annotation within said image, said first annotation input by said first user using an input device and including at least one of a plurality of symbols corresponding to a standardized, pre-defined, graphical language that describes informational content associated with medical findings, wherein said graphical language is predetermined and said informational content is not displayed on said image;

storing said image annotated by said first user, with said at least one symbol thereon in a database;

displaying said image annotated by said first user, to a second user; and receiving and embedding a second annotation within said image, said second annotation input by said second user using another input device, and including at least one of a plurality of additional symbols corresponding to additional information utilizing the standardized graphical language, thereby producing an updated annotated image; and storing said image annotated by said second user, with said at least one symbol thereon, in said database;

wherein a user-selected annotated image containing medically relevant information, is stored separately from other annotated images as a key image in said database, said key image being a representative image that is forwarded to a pre-selected user for separate action by said pre-selected user.

* * * * *